US00PP28680P2

(12) United States Plant Patent
Hansen

(10) Patent No.: US PP28,680 P2
(45) Date of Patent: Nov. 21, 2017

(54) ***PHLOX* PLANT NAMED 'FASHIONABLY EARLY PRINCESS'**

(50) Latin Name: ***Phlox* hybrid**
Varietal Denomination: Fashionably Early Princess

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/530,083

(22) Filed: Dec. 1, 2016

(51) Int. Cl.
*A01H 5/02* (2006.01)

(52) U.S. Cl.
USPC ..... Plt./320

(58) Field of Classification Search
USPC ..... Plt./320
CPC ..... A01H 5/02
See application file for complete search history.

*Primary Examiner* — Kent L Bell

(57) ABSTRACT

A new and unique cultivar of garden *phlox* named *Phlox* 'Fashionably Early Princess' multi-stemmed, dense, slowly-spreading habit with bright-green, glossy, thick-substance, lanceolate leaves. Flowers are sweetly-fragrant, light fuchsia-pink, in many-flowered corymbs beginning very early in early June, continuing for about five weeks and repeating through mid-fall or frost. Foliage stays clean and resists mildew.

1 Drawing Sheet

Botanical classification: *Phlox* hybrid.
Variety denomination: 'Fashionably Early Princess'.

BACKGROUND OF THE INVENTION

The present invention relates to a new and distinct cultivar of *Phlox* plant, known as *Phlox* 'Fashionably Early Princess' and will be referred to hereafter by its cultivar name, 'Fashionably Early Princess', or the "new plant". The new plant was the result of a single seedling selection from the cross of *Phlox maculata* 'Alpha' (not patented) times *Phlox* 'Amethyst Pearl' U.S. Plant patent application Ser. No. 15/330,047 performed at a wholesale perennial nursery in Zeeland, Mich. on Jun. 13, 2012. The new plant was originally given the breeder code 12-11-99 after passing the initial evaluation in the summer of 2013. 'Fashionably Early Princess' has been asexually propagated by stem cuttings in the greenhouses at the same nursery in Zeeland, Mich. The unique characteristics of the new plant have been found to be reproducible and stable in successive generations of asexually propagated plants, and the resultant plants have been found to be identical to the original selection.

No plants of *Phlox* 'Fashionably Early Princess' have been sold, in this country or anywhere in the world, prior to the filing of this application, nor has any disclosure of the new plant been made prior to the filing of this application with the exception of that which may have been disclosed within one year of the filing date of this application and was either derived directly or indirectly from the inventor.

BRIEF SUMMARY OF THE PLANT

*Phlox* 'Fashionably Early Princess' is unique from its parents and all other tall garden *phlox* or other *Phlox* known to the inventor. The new plant differs from the female parent *Phlox* 'Alpha' by having light fuchsia pink flowers with a dark pink eye compared to the white flowers of 'Alpha'. Compared to the male parent 'Amethyst Pearl', the new plant has flowers of a more reddish hue rather than the flowers of 'Amethyst Pearl' with a more purple hue. The nearest comparison variety is the co-pending 'Fashionably Early Flamingo' U.S. Plant patent application Ser, No. 15/530,085, which has a deeper reddish flower, fewer flowers per corymb but more branched and denser corymbs. Compared to co-pending 'Fashionably Early Crystal', U.S. Plant patent application Ser. No. 15/530,082, 'Fashionably Early Flamingo' and 'Fashionably Early Lavender Ice' U.S. Plant patent application Ser. No. 15/530,084, the new plant begins flowering about one week earlier. 'Fashionably Early Princess' differs from all other *phlox* known to the inventor in the following repeatedly observed traits in combination:

1. Plants of compact habit, slowly spreading by short rhizomes, producing clean, glossy, bright-green, lanceolate leaves.
2. Foliage thicker substance than *Phlox paniculata* types showing exceptional powdery mildew resistance.
3. Multiple stems produce elliptic heads of many flowers very early in the season.
4. Sweetly fragrant flowers of light fuchsia-pink on strong flexible stems of about 70 to 80 cm tall.
5. Excellent re-blooming through mid-fall when dead-headed.

BRIEF DESCRIPTION OF THE DRAWINGS

The photographs of the new plant demonstrate the unique traits of 'Fashionably Early Princess' and the overall appearance of the plant at two-years old. The colors are as accurate as reasonably possible with color reproductions. Variation in ambient light spectrum, source and direction may cause the appearance of minor variation in color.

DETAILED BOTANICAL DESCRIPTION

Figure 1:
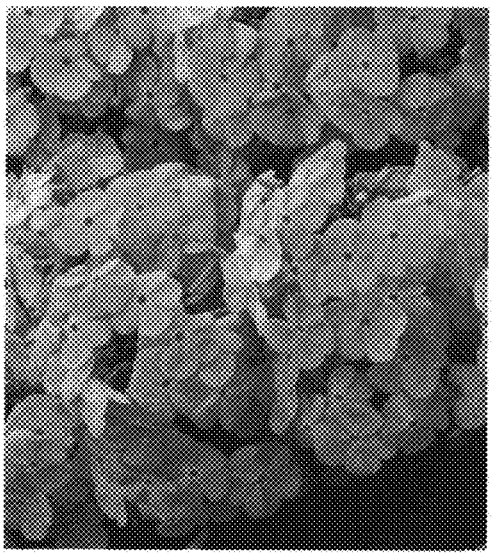
FIG. 1 shows a close-up of the floriferous flower head with flowers and buds.
Figure 2:
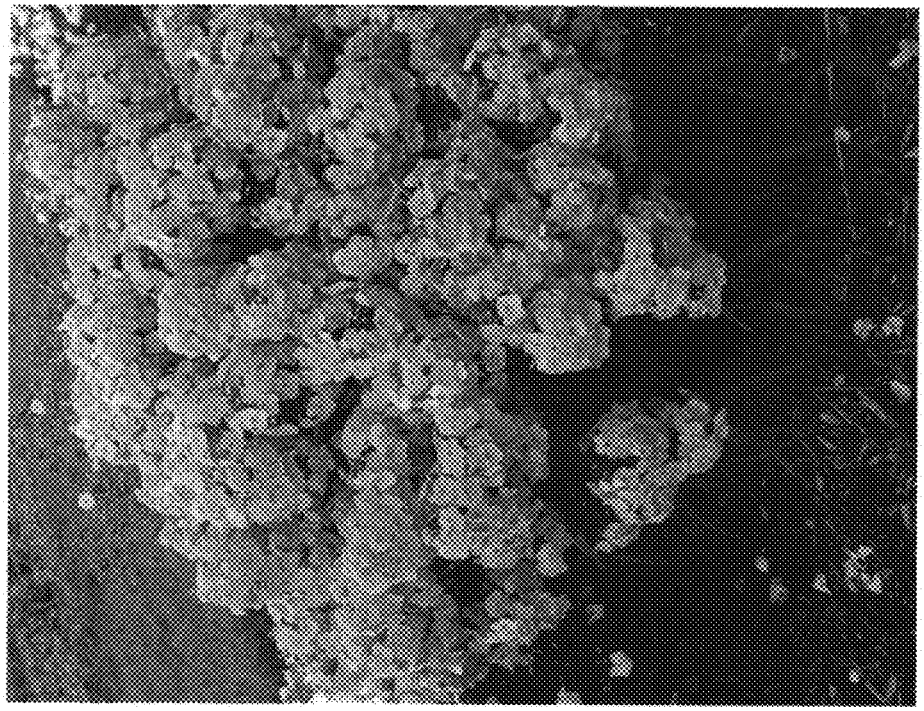
FIG. 2 shows the new plant in flower in the landscape with late spring to early summer foliage.

The following descriptions and color references are based on the 2001 edition of The Royal Horticultural Society Colour Chart except where common dictionary terms are used. *Phlox* 'Fashionably Early Princess' has not been observed under all possible environments. The phenotype may vary slightly with different growing environments such as temperature, light, fertility, soil pH, moisture and maturity levels, but without any change in the genotype. The following observations and size descriptions are based on two-year-old plants in the full sun trial garden of a wholesale perennial nursery in Zeeland, Mich. with supplemental fertilizer and water as needed.

Botanical classification: *Phlox* hybrid.

Parentage: Female or seed parent *Phlox maculata* 'Alpha'; male or pollen parent *Phlox* 'Amethyst Pearl'.

Plant habit: Hardy herbaceous perennial, densely upright, producing about 25 rigid upright stems; about 70 to 80 cm tall at flowering and about 68.0 cm wide at flowers; flowering begins late spring in Michigan and continuing for about 5 weeks and repeating through mid-fall and until heavy frost if deadheaded.

Propagation: Stem cuttings; rooting in about 14 days.

Time to produce finished crop in 3.8 liter pots: About 8 to 10 weeks; moderate rate of growth.

Root: Primary roots to about 1.0 mm thick; secondary fibrous and freely branching; color creamy white to tan depending on soil type glabrous abaxial; puberulent near adaxial vein.

Leaf: Opposite, lanceolate; glabrous abaxial, puberulent near vein adaxial; lustrous adaxial, matte abaxial; acute apex, rounded base; to about 15.5 cm long by about 1.9 cm wide, average about 12.5 cm long by about 18.0 mm wide.

Leaf color at flowering: Abaxial between RHS 146B and RHS 146C; adaxial nearest 141A.

Foliage fragrance: None detected.

Veins: Reticulate; glabrous abaxial, puberulent adaxial; midvein about 1.0 mm wide at base, slightly sunken adaxial and costate abaxial.

Vein color: Abaxial midrib nearest RHS 146A, adaxial midrib between RHS N144A and RHS 146D; other adaxial and abaxial veins same color as surrounding tissue.

Petiole: Short, about 2.0 mm long and 4.0 mm across.

Petiole color: Nearest RHS 146A abaxial and between RHS N144A and RHS 146D adaxial.

Stems: Terete; stiff; strong; upright; sparsely puberulent; average about 68.0 cm long and 4.5 mm diameter at base.

Stem color: Nearest RHS 145A with light speckling of nearest RHS 187B on sun exposed portion.

Nodes: About 10 per stem below flowers; average internode length about 6.8 cm; shorter proximally and longer distally.

Node color: Nearest RHS 145A.

Flowers: Perfect; rotate, salverform, actinomorphic; typically with five petals; about 2.9 cm long total, with tube about 2.8 cm long and 2.5 mm diameter before face and 2.0 mm diameter at base; face about 3.1 cm across; held in a branched compound corymb of about 190 to 270 flowers; attitude upright to outward.

Flower longevity: About 5 days on plant or as cut flower; self-cleaning.

Flower flagrance: Pleasantly sweet.

Buds one to two days prior to opening: Narrowly oblanceolate, to nearly clavate; acute apex with petals twisted about each other; about 2.3 cm long and 2.5 mm diameter in tube and swollen to 4.0 mm diameter toward apex.

Bud color: Tube base nearest 145C, tube center nearest RHS 145C; swollen apex nearest RHS N87B and bulb base nearest RHS N87D.

Petals: Five, glabrous except pubescent for about 4.0 mm to 6.5 mm from base of adaxial tube; margin entire; apex rounded; basal 2.9 cm fused into tube; face to about 1.5 cm across; adaxial about 10.0 mm of tube throat, rounded limbs with rounded apex; limbs about 1.4 cm across, imbricate about 3.5 mm of the petals to either side.

Young petal color: Abaxial tube base nearest RHS 150D, abaxial tube middle nearest RHS 84C, abaxial face lighter than RHS N82D, abaxial face perimeter nearest RHS N81C, surrounding throat nearest RHS 76A; adaxial face nearest RHS N80B, throat radiating star lighter than RHS 84D with gradual lightening toward margin, tube base nearest RHS 150D, tube middle nearest RHS 84C.

Mature petal color: Abaxial tube nearest RHS 84B, abaxial face nearest RHS 84C; adaxial tube nearest RHS 150D at base and RHS 84B in middle, adaxial face nearest RHS 84D with center portions of petal covered by other imbricate petals blend of RHS N74B and RHS N78B.

Androecium: Typically five.

*Filaments*.—Five, fused to inner petals except free in terminal 1.0 mm; varying lengths between 15.0 mm and 20.0 mm above base, less than 0.2 mm in diameter; color white, lighter than RHS 155D.

*Anther*.—Five; oblong elliptic; semi-basifixed; longitudinal; joined at different heights about 2.0 mm, 2.3 mm and 2.5 mm above base; about 3.0 mm long by 1.0 mm wide; color nearest RHS 13B.

*Pollen*.—Nearly microscopic; abundant; spherical; color nearest RHS 17B.

Gynoecium: One pistil per flower.

*Style*.—Terete; about 2.2 cm long and 0.3 mm diameter when flower is mature; color nearest RHS 145C.

*Stigma*.—Trifurcate in the distal 2 mm, less than 0.25 mm in diameter; persistent after flower abscission; nearest RHS 6B.

*Ovary*.—Superior; elliptic with slight acute apex; about 2.0 mm long and 1.0 mm diameter; color nearest RHS 145A.

Sepals: Five, glabrous; lanceolate; sharply acute apex, margin entire; individually about 10.5 mm long and 2.5 mm wide; fused in basal 7.0 mm forming tube 2.5 mm diameter at base and 3.5 mm diameter at apex.

Sepal color: Abaxial apical 0.5 mm nearest RHS 187A, midsection nearest RHS 138B to RHS N186C in high light exposure, margins (about 0.5 mm wide) translucent with some pigment nearest RHS 187D; adaxial apex nearest RHS 187A, center nearest RHS 138B with slight blush tinting nearest RHS 187B, margins (about 0.5 mm wide) translucent with some blush nearest RHS 187D.

Peduncle: Puberulent, stiff, strong, upright, terete; about 4.0 mm diameter at base of main flower stem and 2.0 mm diameter of branches; flowering portion ellipsoidal, about 10.0 cm long with flowers spreading 8.0 cm across the inflorescence.

Peduncle color: Between RHS 145A and RHS 146D with heavy speckling nearest RHS 187B on areas of heavy sun exposure.

Fruit and seed have not yet been observed.

Hardiness and culture: The new plant grows best with plenty of moisture and adequate drainage; hardy to at least from USDA zone 4 through 8.

Disease and pest resistance: *Phlox* 'Fashionably Early Princess' demonstrated the excellent powdery mildew resistance under conditions that would normally show symptoms.

It is claimed:

1. A new and distinct cultivar of hybrid *phlox* plant named *Phlox* 'Fashionably Early Princess', as herein described and illustrated.

* * * * *